(12) United States Patent
Cao et al.

(10) Patent No.: US 11,852,760 B2
(45) Date of Patent: Dec. 26, 2023

(54) IMAGE SENSOR WITH RADIATION DETECTORS AND A COLLIMATOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 130 days.

(21) Appl. No.: 17/471,840

(22) Filed: Sep. 10, 2021

(65) Prior Publication Data
US 2021/0405222 A1 Dec. 30, 2021

Related U.S. Application Data

(63) Continuation of application No. PCT/CN2019/080410, filed on Mar. 29, 2019.

(51) Int. Cl.
*G01T 1/24* (2006.01)
*G02B 27/30* (2006.01)
*H01L 27/146* (2006.01)

(52) U.S. Cl.
CPC .............. *G01T 1/241* (2013.01); *G01T 1/244* (2013.01); *G02B 27/30* (2013.01); *H01L 27/14658* (2013.01)

(58) Field of Classification Search
CPC ......... G01T 1/241; G01T 1/244; G02B 27/30; H01L 27/14658
See application file for complete search history.

(56) References Cited

U.S. PATENT DOCUMENTS

| 6,035,013 | A | 3/2000 | Orava et al. | |
|---|---|---|---|---|
| 6,236,051 | B1* | 5/2001 | Yamakawa | G01T 1/2928 250/370.1 |
| 2008/0135765 | A1 | 6/2008 | Vydrin | |
| 2013/0114790 | A1 | 5/2013 | Fabrizio | |
| 2014/0064446 | A1* | 3/2014 | Wear | G01N 23/04 250/366 |
| 2015/0065873 | A1* | 3/2015 | Tsukerman | A61B 6/4447 600/436 |

(Continued)

FOREIGN PATENT DOCUMENTS

| CN | 101500488 A | 8/2009 |
|---|---|---|
| CN | 102401906 A | 4/2012 |
| CN | 103784154 A | 5/2014 |

(Continued)

*Primary Examiner* — David P Porta
*Assistant Examiner* — Fani Polyzos Boosalis
(74) *Attorney, Agent, or Firm* — IPRO, PLLC; Qian Gu

(57) ABSTRACT

Disclosed herein is a method comprising: aligning a collimator and a plurality of radiation detectors of an image sensor by: moving the radiation detectors along a first direction; moving the collimator along a second direction perpendicular to the first direction; rotating the collimator about an axis perpendicular to the first direction and the second direction; wherein the plurality of radiation detectors are configured to capture images of portions of a scene at different image capturing positions, respectively, and to form an image of the scene by stitching the images of the portions.

17 Claims, 16 Drawing Sheets

(56) References Cited

U.S. PATENT DOCUMENTS

2016/0310098 A1* 10/2016 Kim ................. A61B 6/544
2020/0257007 A1* 8/2020 Hermony ........... A61B 6/037

FOREIGN PATENT DOCUMENTS

| | | | | | |
|---|---|---|---|---|---|
| CN | 106793990 | A | | 5/2017 | |
| CN | 206648976 | U | | 11/2017 | |
| CN | 113287299 | A | * | 8/2021 | ............ A61B 6/032 |
| JP | 2010094498 | A | | 4/2010 | |
| TW | 201910808 | A | | 3/2019 | |
| WO | 2018112721 | A1 | | 6/2018 | |

* cited by examiner

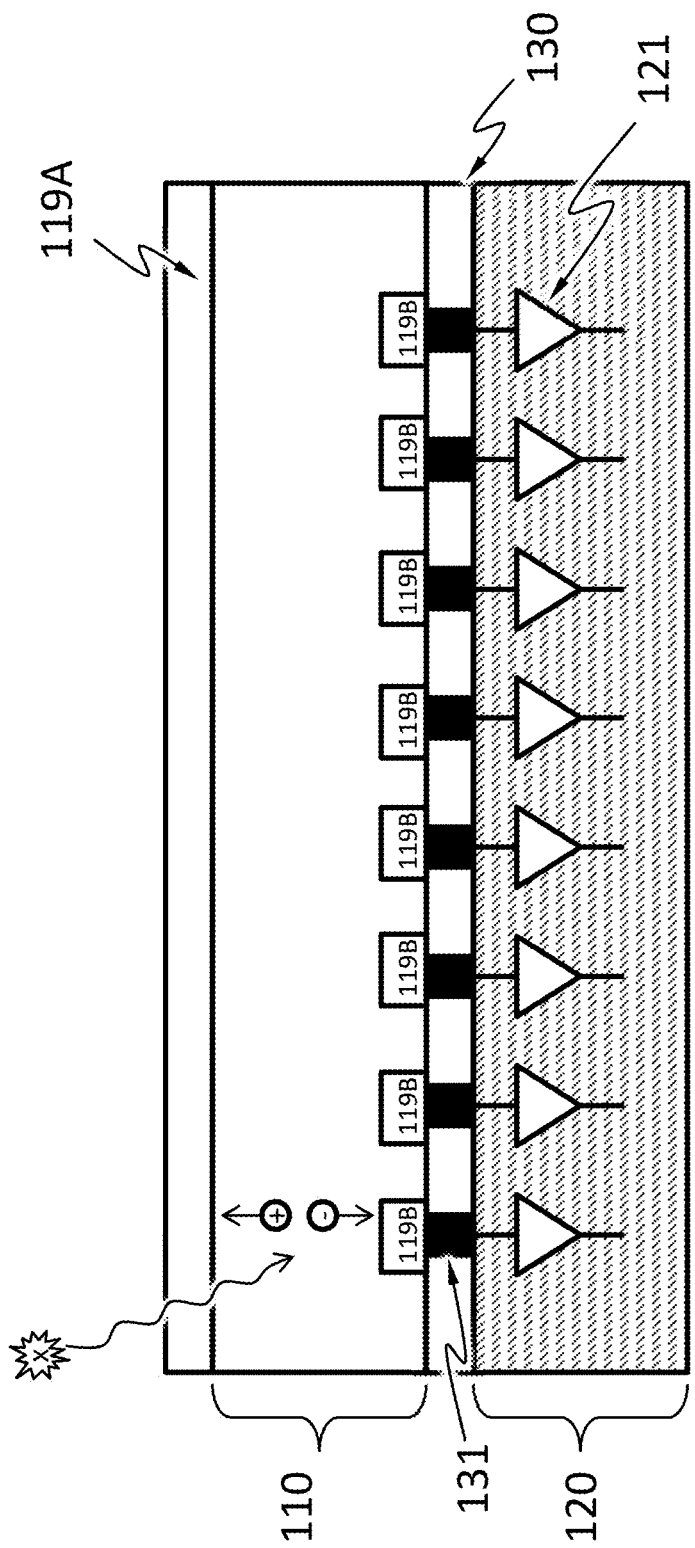

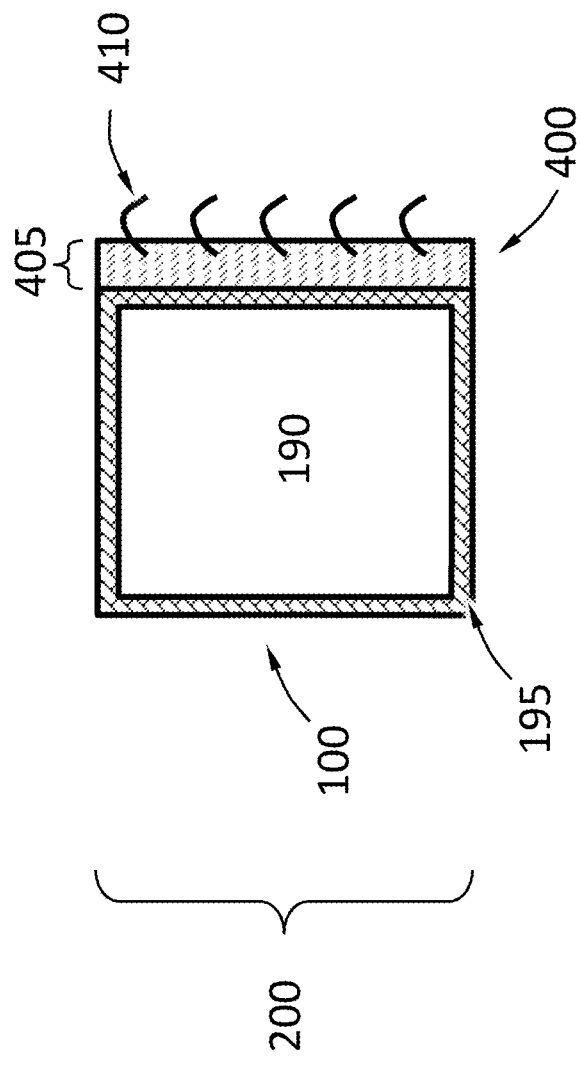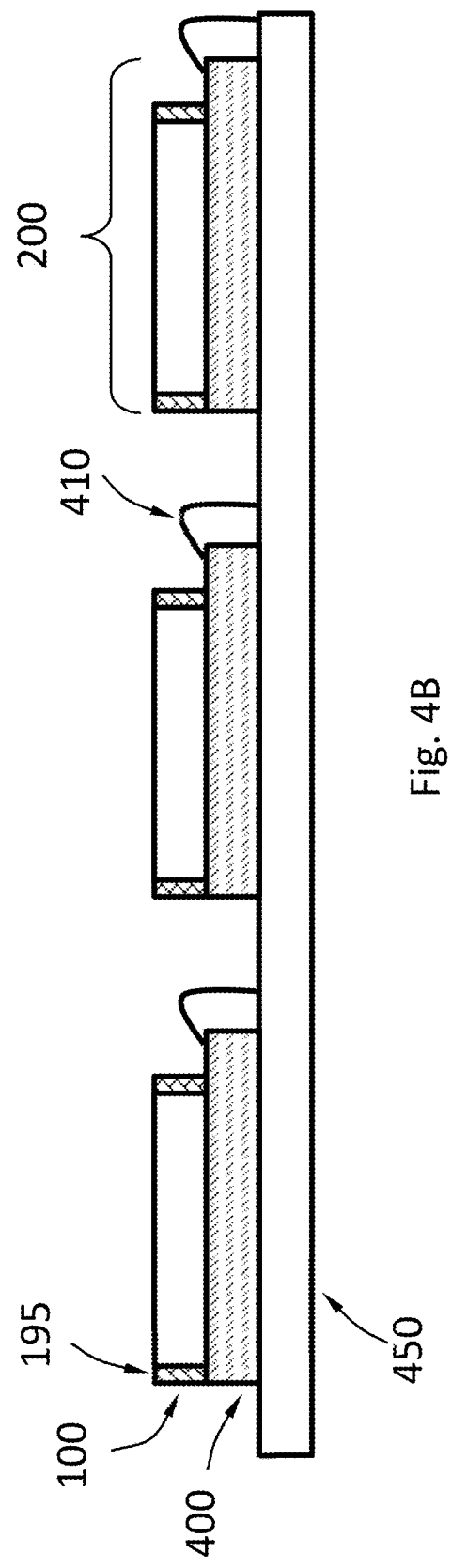

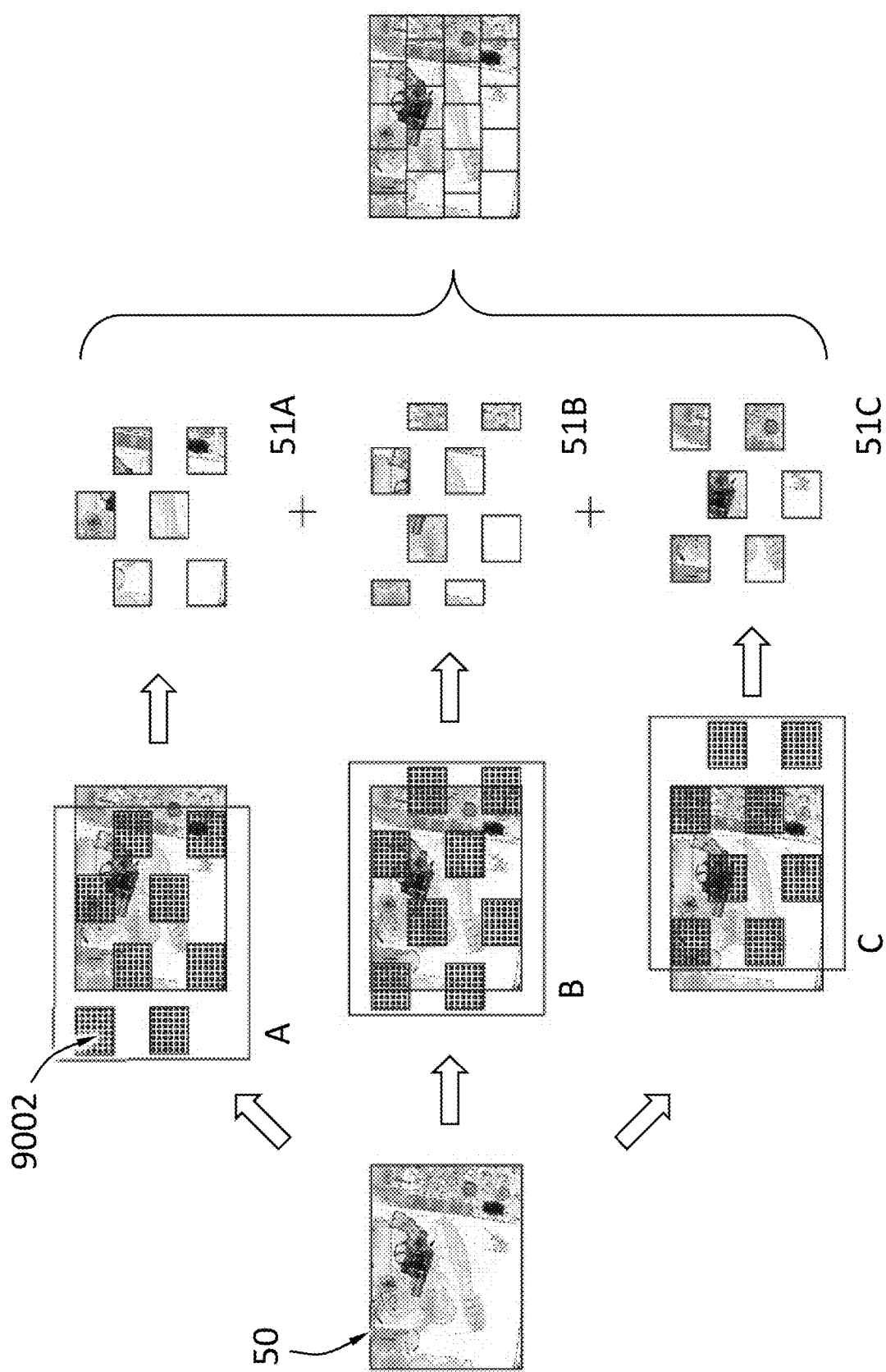

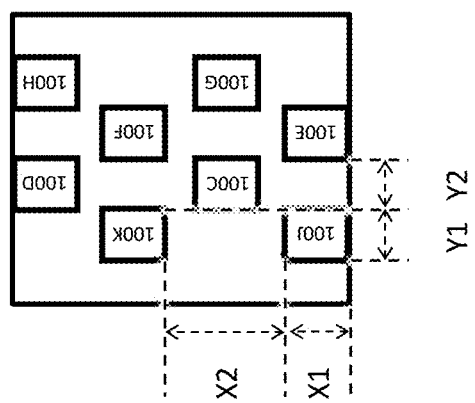
Fig. 9A
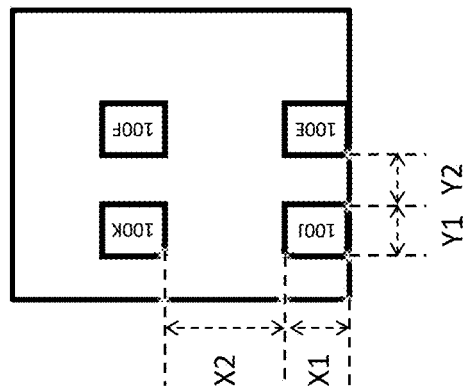
Fig. 9B
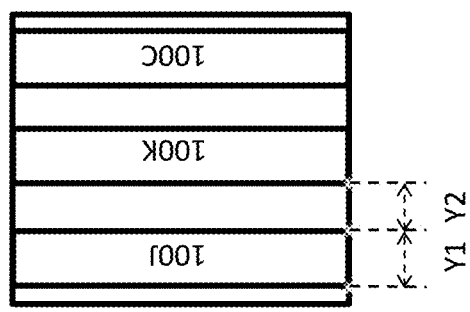
Fig. 9C
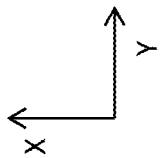

IMAGE SENSOR WITH RADIATION DETECTORS AND A COLLIMATOR

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, Radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident Radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a radiation particle is absorbed in the semiconductor layer, multiple charge carriers (e.g., electrons and holes) are generated and swept under an electric field towards electric contacts on the semiconductor layer. Cumbersome heat management required in currently available semiconductor radiation detectors (e.g., Medipix) can make a detector with a large area and a large number of pixels difficult or impossible to produce.

SUMMARY

Disclosed herein is a method comprising: aligning a collimator and a plurality of radiation detectors of an image sensor by: moving the radiation detectors along a first direction; moving the collimator along a second direction perpendicular to the first direction; rotating the collimator about an axis perpendicular to the first direction and the second direction; wherein the plurality of radiation detectors are configured to capture images of portions of a scene at different image capturing positions, respectively, and to form an image of the scene by stitching the images of the portions.

According to an embodiment, the image capturing positions are displaced from one another along the first direction.

According to an embodiment, the collimator includes a plurality of radiation transmitting zones and a radiation blocking zone, and wherein, when the collimator is aligned with the radiation detectors, the radiation blocking zone substantially blocks radiation that would otherwise incident on a dead zone of the image sensor and the radiation transmitting zones allow transmission of at least a portion of the radiation that would incident on active areas of the image sensor.

According to an embodiment, the method further comprises moving the plurality of radiation detectors among the image capturing positions.

According to an embodiment, at least some of the plurality of radiation detectors are arranged in staggered rows.

According to an embodiment, active areas of the plurality of radiation detectors tessellate the scene at the image capturing positions.

According to an embodiment, the images of portions of the scene at the different image capturing positions have a spatial overlap.

According to an embodiment, the plurality of radiation detectors include a first radiation detector and a second radiation detector, respectively comprising a planar surface configured to receive radiation from a radiation source, and the planar surface of the first radiation detector and the planar surface of the second radiation detector are not parallel.

Disclosed herein is an image sensor comprising: a plurality of radiation detectors; a collimator; and an actuator configured to: move the radiation detectors along a first direction; move the collimator along a second direction perpendicular to the first direction; rotate the collimator about an axis perpendicular to the first direction and the second direction; wherein the plurality of radiation detectors are configured to capture images of portions of a scene at different image capturing positions, respectively, and to form an image of the scene by stitching the images of the portions.

According to an embodiment, the image capturing positions are displaced from one another along the first direction.

According to an embodiment, the collimator includes a plurality of radiation transmitting zones and a radiation blocking zone, and wherein, when the collimator is aligned with the radiation detectors, the radiation blocking zone substantially blocks radiation that would otherwise incident on a dead zone of the image sensor and the radiation transmitting zones allow transmission of at least a portion of the radiation that would incident on active areas of the image sensor.

According to an embodiment, at least some of the plurality of radiation detectors are arranged in staggered rows.

According to an embodiment, active areas of the plurality of radiation detectors tessellate the scene at the positions.

According to an embodiment, the images of portions of the scene at the different image capturing positions have a spatial overlap.

According to an embodiment, the plurality of radiation detectors include a first radiation detector and a second radiation detector, respectively comprising a planar surface configured to receive radiation from a radiation source, and the planar surface of the first radiation detector and the planar surface of the second radiation detector are not parallel.

According to an embodiment, a relative position of the first radiation detector with respect to the second radiation detector remains the same.

Also disclosed herein is a radiation computed tomography system comprising: the image sensor above, and a radiation source.

BRIEF DESCRIPTION OF FIGURES

FIG. 2C schematically shows an alternative detailed cross-sectional view of the radiation detector, according to an embodiment.

FIG. 4A schematically shows a top view of a package including the radiation detector and a printed circuit board (PCB).

FIG. 4B schematically shows a cross-sectional view of the image sensor, where a plurality of the packages of FIG. 4A are mounted to another PCB.

FIG. 8 schematically shows the image of an object can be formed by stitching images of multiple different portions of an object, according to an embodiment.

FIG. 9A-FIG. 9D schematically show arrangements of the radiation detectors in the image sensor, according to some embodiments.

DETAILED DESCRIPTION

Figure 1:
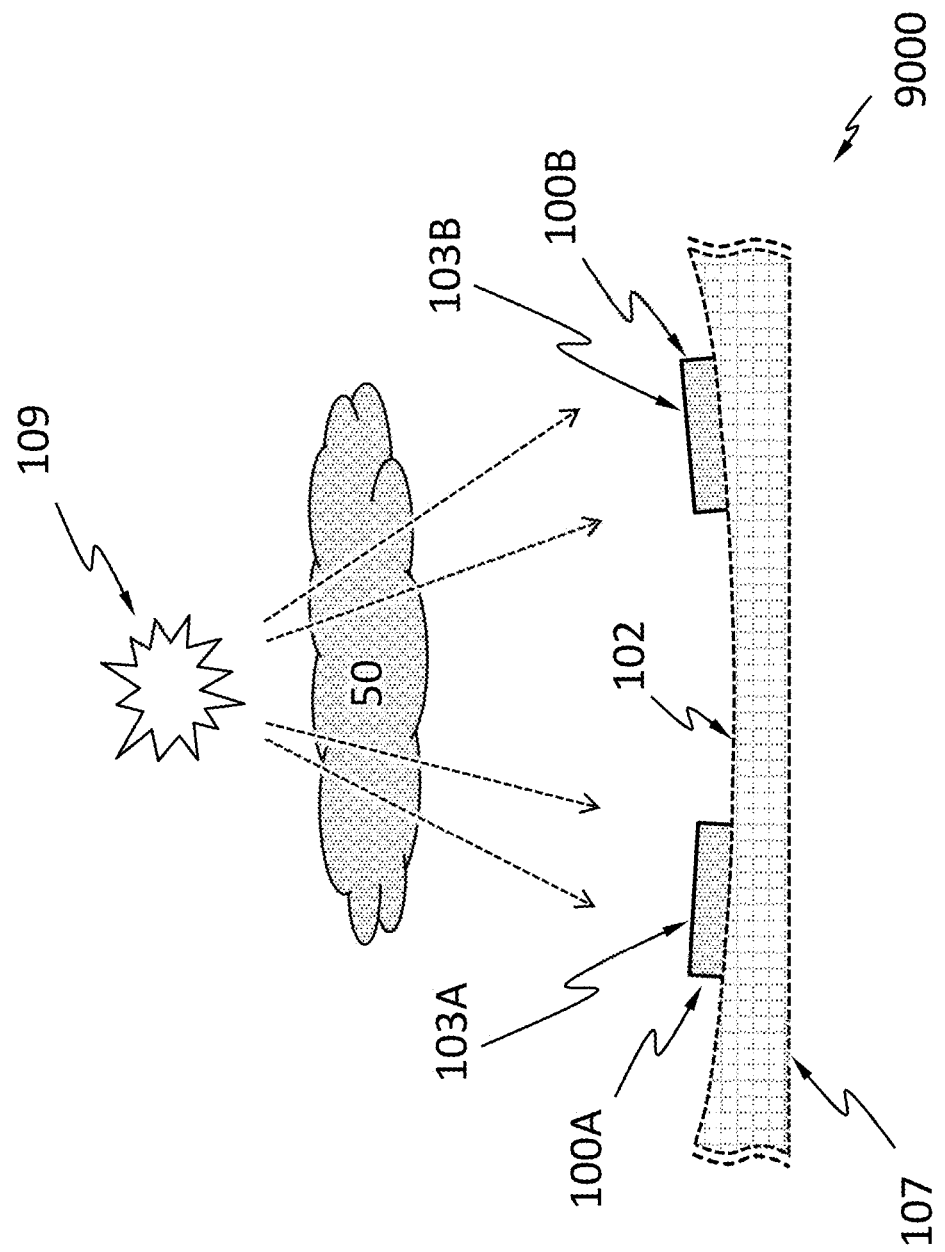
FIG. 1 schematically shows a cross-sectional view of a portion of an image sensor, according to an embodiment.

FIG. 1 schematically shows a cross-sectional view of a portion of an image sensor 9000, according to an embodiment. The image sensor 9000 may have a plurality of radiation detectors 100 (e.g., a first radiation detector 100A, a second radiation detector 100B). The radiation detectors 100 may be spaced apart from one another in the image sensor 9000. The image sensor 9000 may have a support 107. The support 107 may have a curved surface 102. The plurality of radiation detectors 100 may be arranged on the support 107, for example, on the curved surface 102, as shown in the example of FIG. 1. The first radiation detector 100A may have a first planar surface 103A configured to receive radiation from a radiation source 109. A second radiation detector 100B may have a second planar surface 103B configured to receive the radiation from the radiation source 109. The first planar surface 103A and the second planar surface 103B may be not parallel. The radiation from the radiation source 109 may have passed through a scene 50 (e.g., a portion of a human body) before reaching the first radiation detector 100A or the second radiation detector 100B.

Figure 2A:
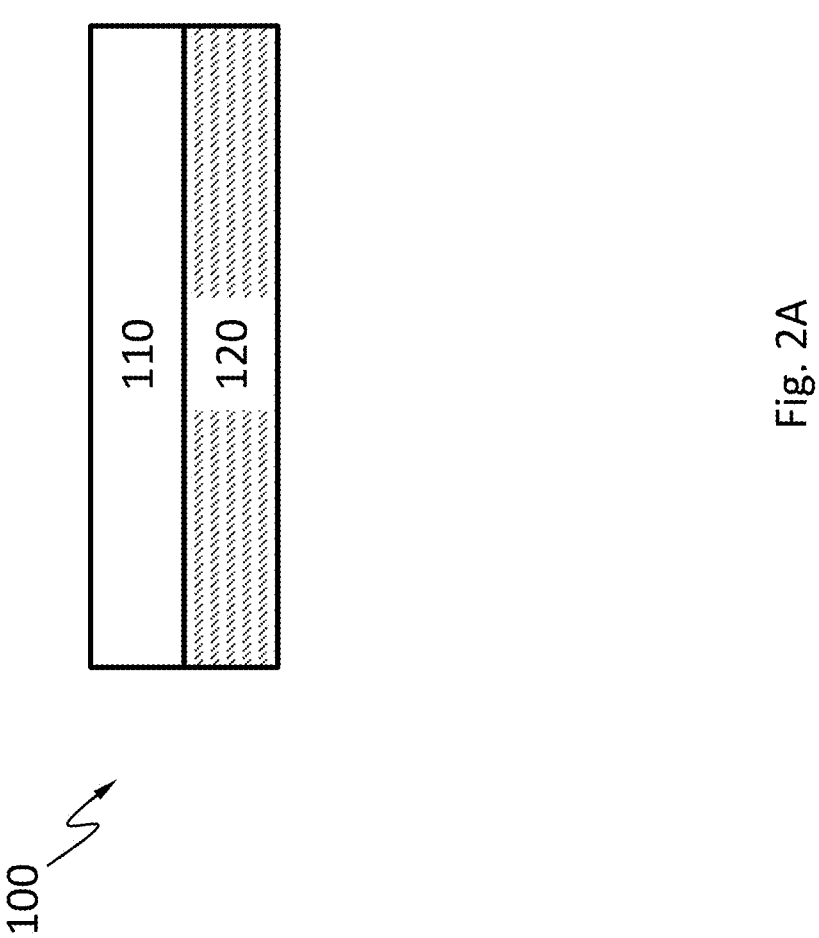
FIG. 2A schematically shows a cross-sectional view of a radiation detector of the image sensor, according to an embodiment.

FIG. 2A schematically shows a cross-sectional view of one radiation detector 100 of the image sensor 9000, according to an embodiment. The radiation detector 100 may include a radiation absorption layer 110 and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a semiconductor material such as silicon, germanium, GaAs, CdTe, CdZnTe, or a combination thereof. The semiconductor may have a high mass attenuation coefficient for the radiation produced by the radiation source 109.

Figure 2B:
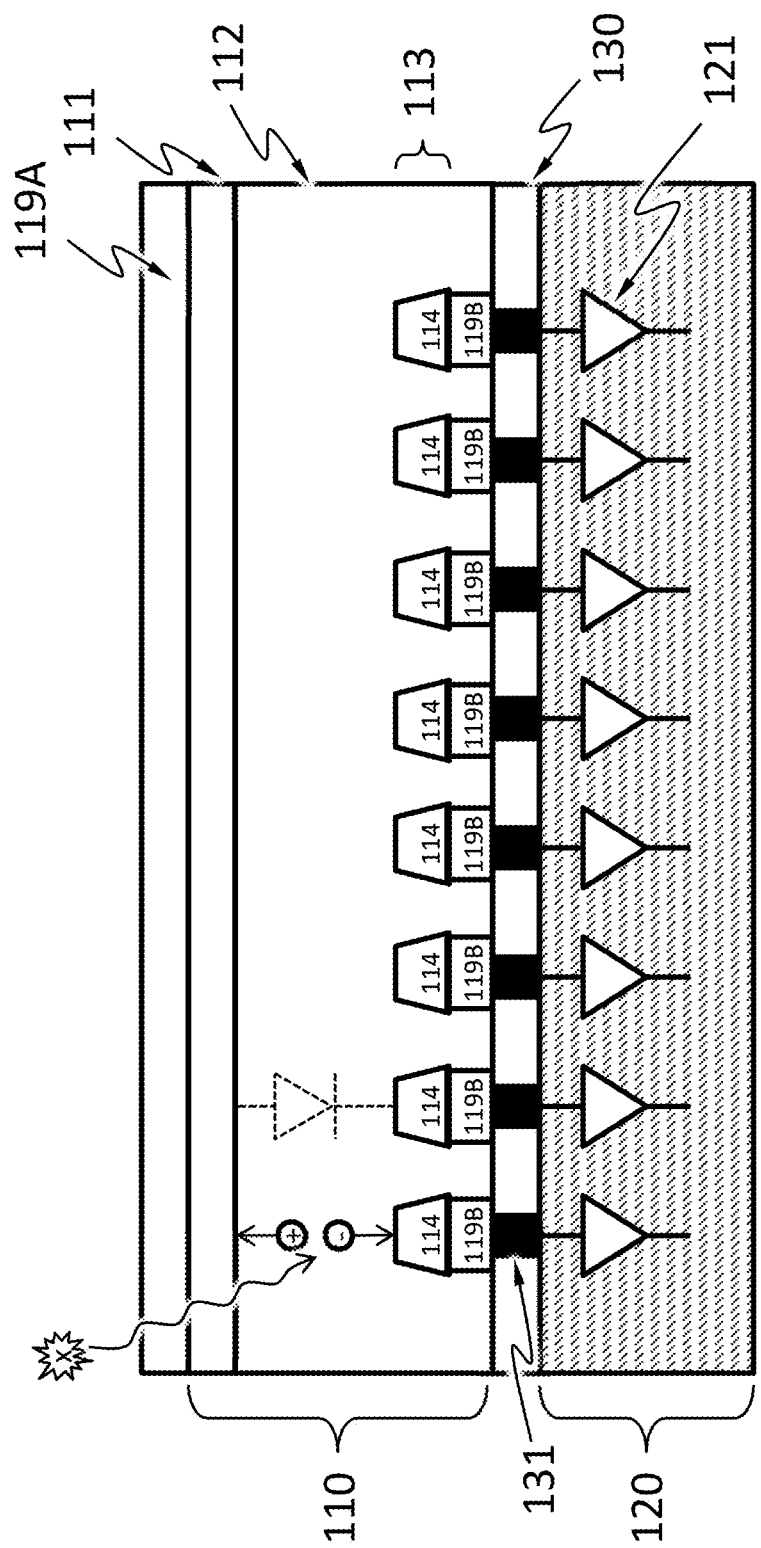
FIG. 2B schematically shows a detailed cross-sectional view of the radiation detector, according to an embodiment.

As shown in a detailed cross-sectional view of the radiation detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When a particle of radiation hits the radiation absorption layer 110 including diodes, the particle of radiation may be absorbed and generate one or more charge carriers by a number of mechanisms. A particle of radiation may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of radiation incident therein flow to the discrete region 114. Namely, less than 2%, less than 1%, less than 0.1%, or less than 0.01% of these charge carriers flow beyond the pixel.

As shown in an alternative detailed cross-sectional view of the radiation detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation produced by the radiation source 109.

When a particle of radiation hits the radiation absorption layer 110 including a resistor but not diodes, it may be absorbed and generate one or more charge carriers by a number of mechanisms. A particle of radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by particles of radiation incident on the radiation absorption layer 110. The electronic system 121 may include an analog circuitry such as a filter network, amplifiers, integrators, and comparators, or a digital circuit such as a microprocessor and a memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 3:
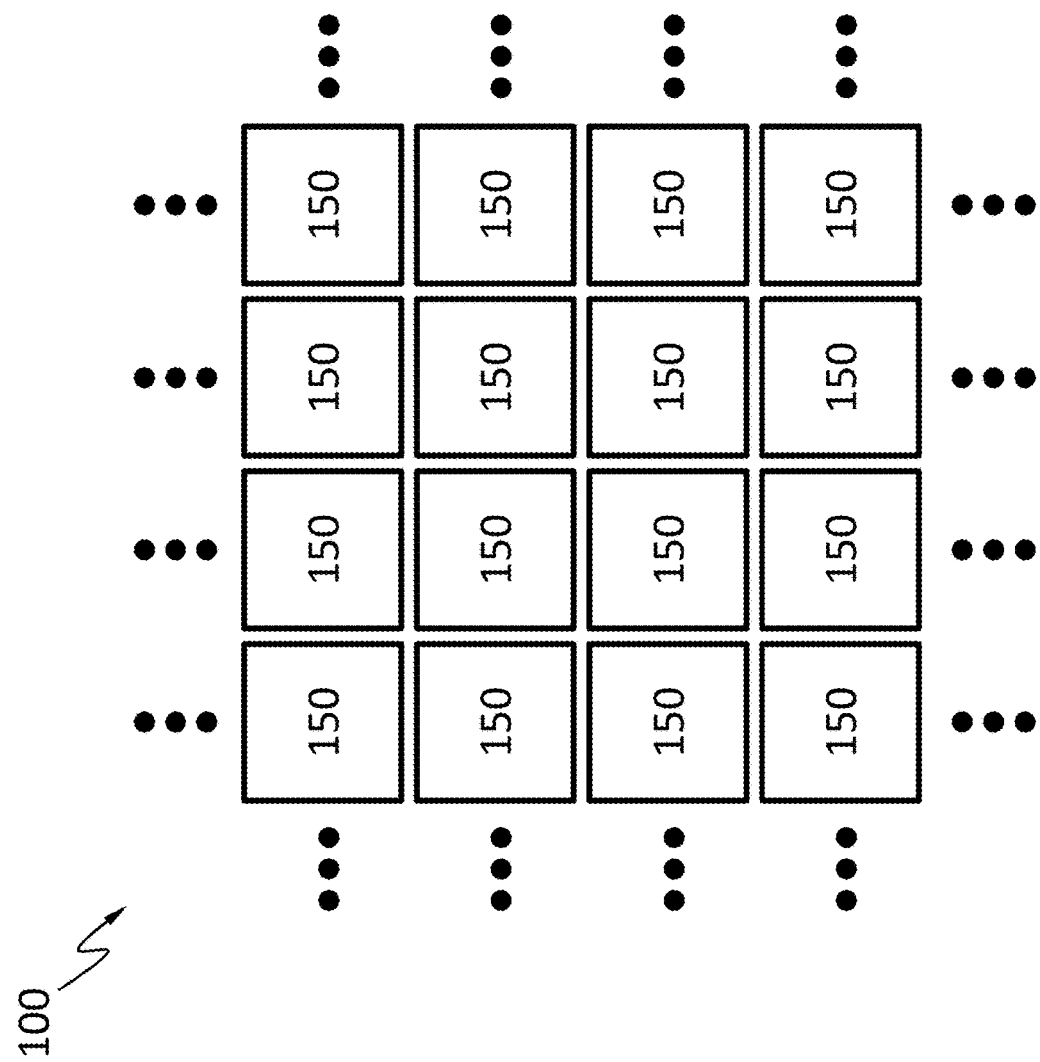
FIG. 3 schematically shows that the radiation detector may have an array of pixels, according to an embodiment.

FIG. 3 schematically shows that the radiation detector 100 may have an array of pixels 150. The array may be a rectangular array, a honeycomb array, a hexagonal array or any other suitable array. Each pixel 150 may be configured to detect a particle of radiation incident thereon, measure the energy of the particle of radiation, or both. For example, each pixel 150 may be configured to count numbers of particles of radiation incident thereon whose energy falls in a plurality of bins, within a period of time. All the pixels 150 may be configured to count the numbers of particles of radiation incident thereon within a plurality of bins of energy within the same period of time. Each pixel 150 may have its own analog-to-digital converter (ADC) configured to digitize an analog signal representing the energy of an incident particle of radiation into a digital signal. The ADC may have a resolution of 10 bits or higher. Each pixel 150 may be configured to measure its dark current, such as before or concurrently with each particle of radiation incident thereon. Each pixel 150 may be configured to deduct the contribution of the dark current from the energy of the particle of radiation incident thereon. The pixels 150 may be configured to operate in parallel. For example, when one pixel 150 measures an incident particle of radiation, another pixel 150 may be waiting for a particle of radiation to arrive. The pixels 150 may be but do not have to be individually addressable.

FIG. 4A schematically shows that one or more of the radiation detectors 100 may be mounted on a printed circuit board (PCB) 400. The term "PCB" as used herein is not limited to a particular material. For example, a PCB may include a semiconductor. The wiring between the radiation detectors 100 and the PCB 400 is not shown for the sake of clarity. The PCB 400 and the radiation detectors 100 mounted thereon may be called a package 200. The PCB 400 may have an area not covered by the radiation detectors 100 (e.g., an area for accommodating bonding wires 410). Each of the radiation detector 100 may have an active area 190, which is where the pixels 150 are located. Each of the radiation detectors 100 may have a perimeter zone 195 near the edges. The perimeter zone 195 has no pixels and particles of radiation incident on the perimeter zone 195 are not detected.

FIG. 4B schematically shows that the image sensor 9000 may have a system PCB 450 with multiple packages 200 mounted on it. The image sensor 9000 may include one or more such system PCBs 450. The electrical connection between the PCBs 400 in the packages 200 and the system PCB 450 may be made by bonding wires 410. In order to accommodate the bonding wires 410 on the PCB 400, the PCB 400 has an area 405 not covered by the radiation detectors 100. In order to accommodate the bonding wires 410 on the system PCB 450, the packages 200 have gaps in between. The active areas 190 of the radiation detectors 100 in the image sensor 9000 are collectively called the active area of the image sensor 9000. The other areas of the image sensor 9000, radiation incident on which cannot be detected by the image sensor 9000, such as the perimeter zones 195, the area 405 or the gaps between the packages 200, are collectively called the dead zone of the image sensor 9000. The radiation detectors 100A and 100B shown in FIG. 1 may be embodiments of the radiation detector 100 and mounted on respective PCB 400 as shown in FIG. 4A in a similar manner, and the support 107 may be part of the PCB 400 in one embodiment or part of the system PCB 450 in another embodiment.

Figure 5:
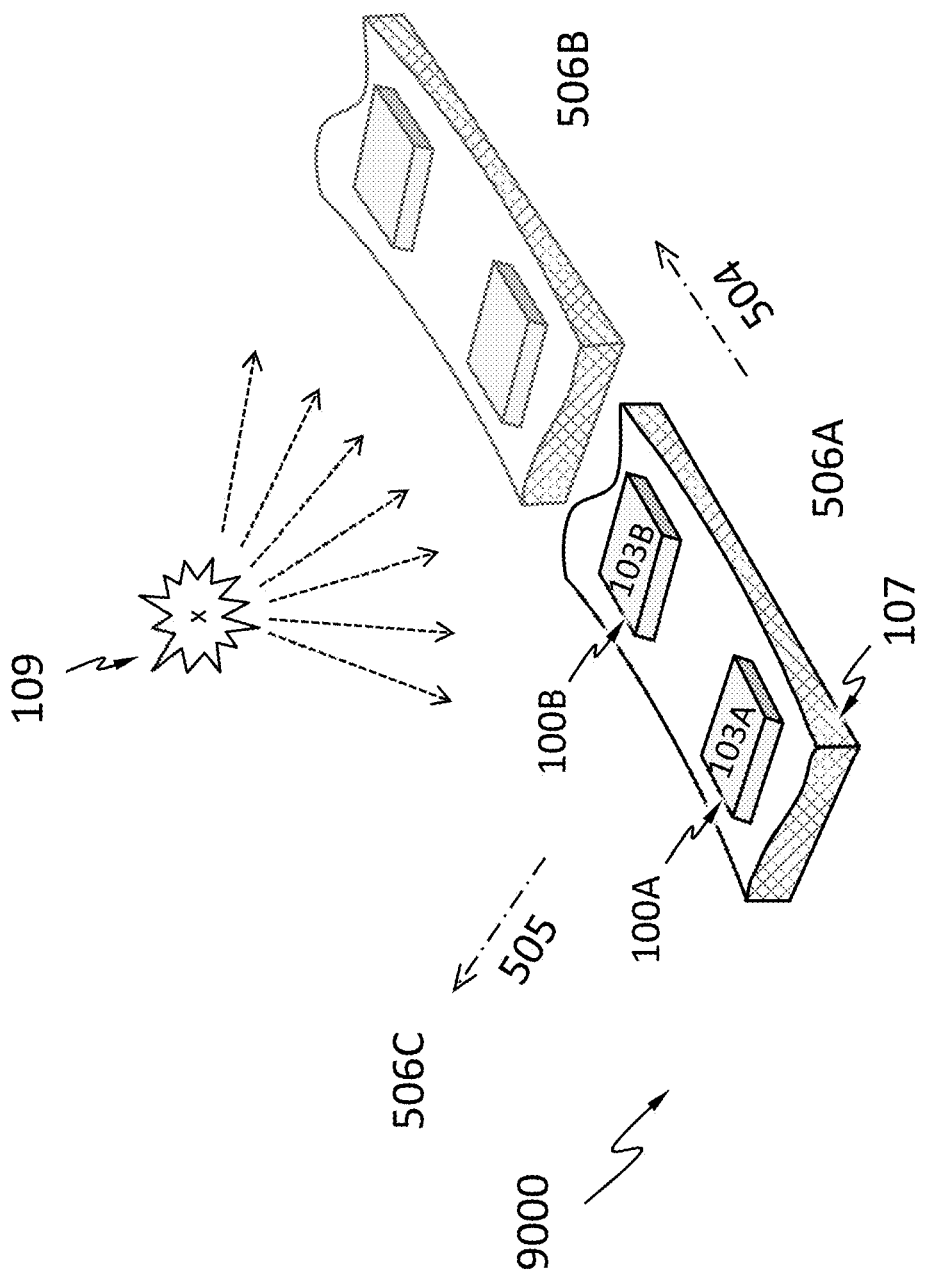
FIG. 5 schematically shows movements of detectors of the image sensor relative to a radiation source, according to an embodiment.

FIG. 5 schematically shows movements of the radiation detectors 100 (e.g., 100A and 100B) relative to the radiation source 109, according to an embodiment. In the examples of FIG. 5, only a portion of the image sensor 9000 with the first radiation detector 100A and the second radiation detector 100B is shown. The first radiation detector 100A and the second radiation detector 100B may be arranged on the support 107. A relative position of the first radiation detector 100A with respect to the second radiation detector 100B remains the same at the multiple positions. The relative position of the first radiation detector 100A with respect to the second radiation detector 100B may but does not necessarily remain the same while they move from one of the multiple positions to another.

As shown in the example of FIG. 5, the first radiation detector 100A and the second radiation detector 100B translate along a first direction 504 from position 506A to position 506B, relative to the radiation source 109. The first radiation detector 100A and the second radiation detector 100B may translate along a second direction 505. The second direction 505 is different from the first direction 504. For example, the second direction 505 may be perpendicular to the first direction 504. As shown in the example of FIG. 5, the first radiation detector 100A and the second radiation detector 100B can translate from position 506A to position 506C, along the second direction 505. The first direction 504 or the second direction 505 may be parallel to both, either or neither of the first planar surface 103A and the second planar surface 103B. For example, the first direction 504 may be parallel to the first planar surface 103A, but not parallel to the second planar surface 103B.

Figure 6:
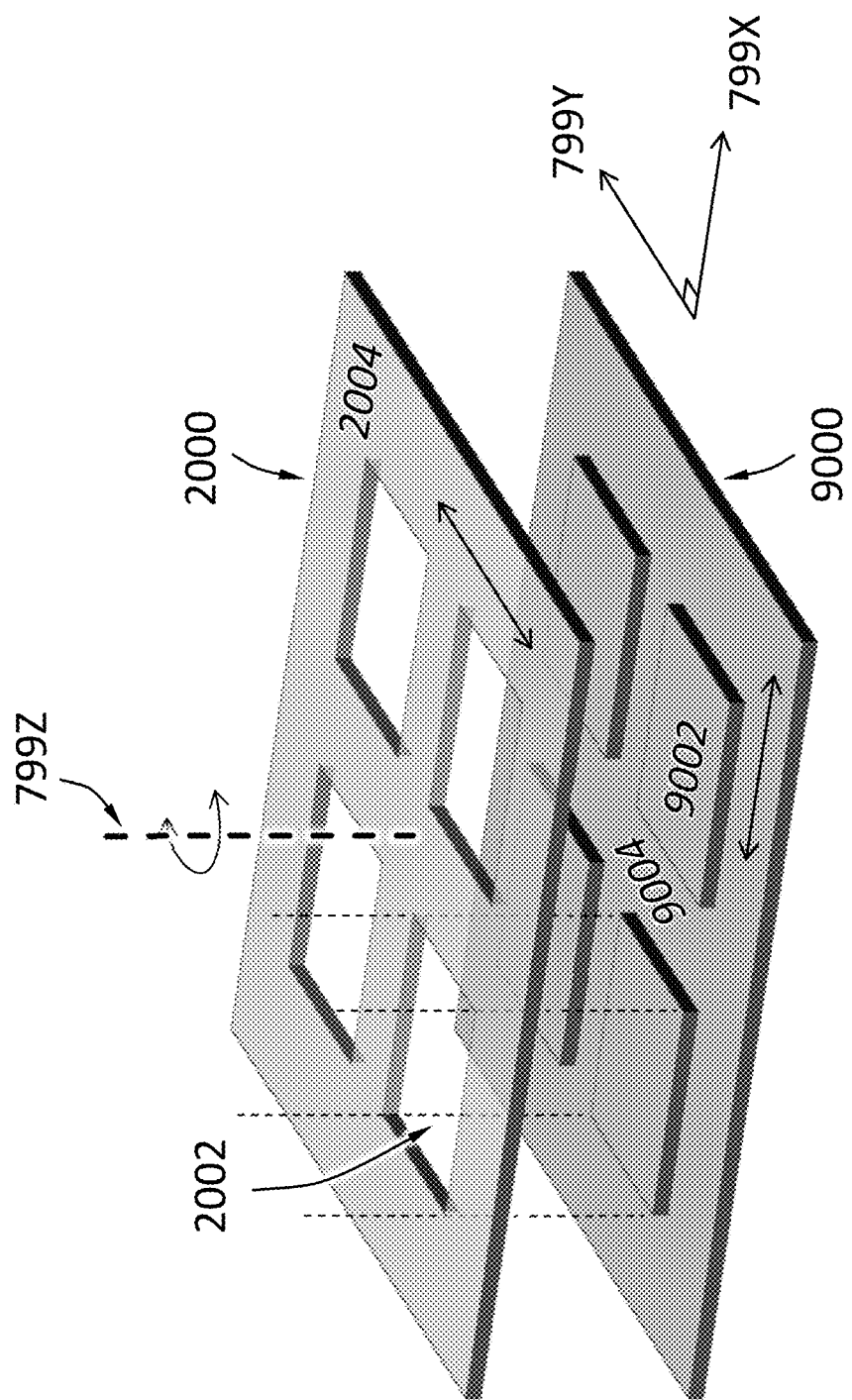
FIG. 6 schematically shows a collimator of the image sensor, according to an embodiment.

FIG. 6 schematically shows that the image sensor 9000 may comprise a collimator 2000. The collimator 2000 comprises a plurality of radiation transmitting zones 2002 and a radiation blocking zone 2004, according to an embodiment. The radiation blocking zone 2004 substantially blocks radiation that would otherwise incident on the dead zone 9004 of the image sensor 9000, and the radiation transmitting zones 2002 allow at least a portion of radiation that would incident on the active areas 9002 of the image sensor 9000 to pass. The radiation transmitting zones 2002 may be holes through the collimator 2000 and the rest of the collimator 2000 may function as the radiation blocking zone 2004. The collimator 2000 may be disposed close to the radiation detectors 100 or away from the radiation detectors 100. For example, the scene 50 may be between the collimator 2000 and the radiation detectors 100. The radiation transmitting zones 2002 may have different sizes or positions from those of the active areas 9002.

The relative position of the collimator 2000 and the radiation detectors 100 may not be fixed. For example, if the radiation from the radiation source 109 is not parallel rays, different relative positions of the collimator 2000 and the radiation detectors 100 may be needed to keep the radiation transmitting zones 2002 aligned with the active areas 9002 when the image sensor 9000 are at different positions relative to the radiation source 109.

Figure 7:
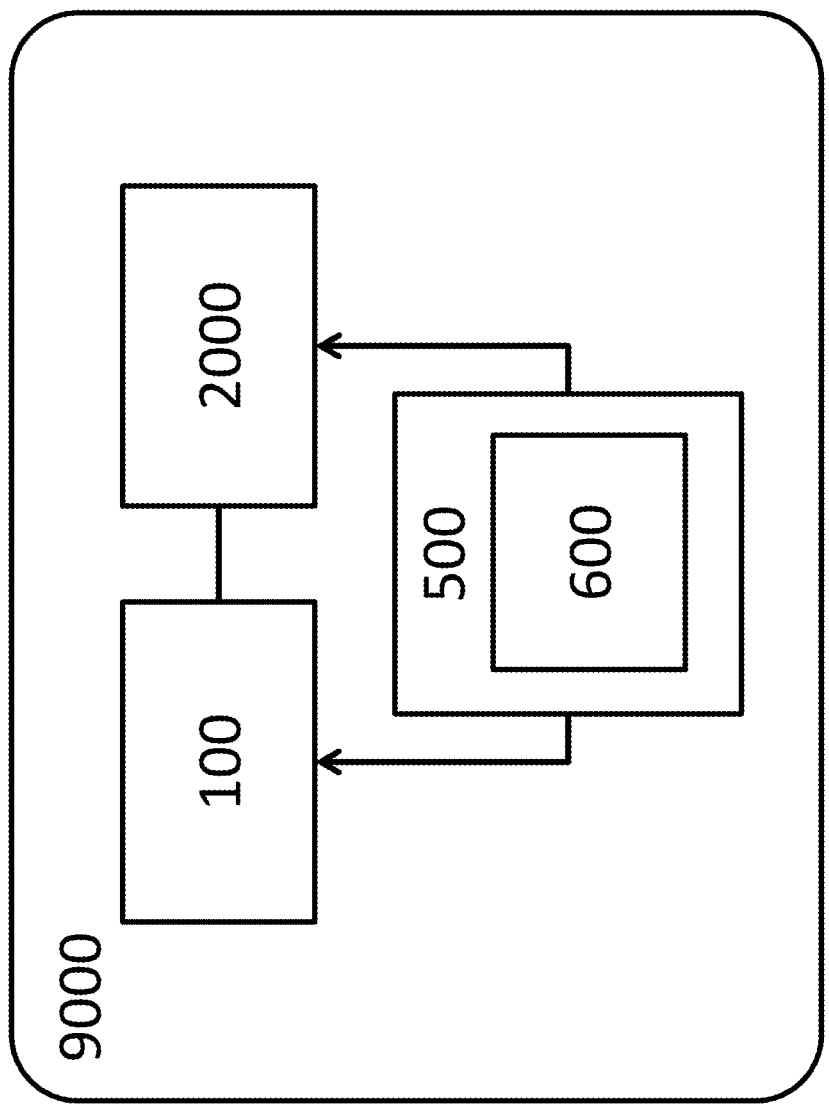
FIG. 7 schematically shows a functional block diagram of the image sensor, according to an embodiment.

In an embodiment, the radiation detectors 100 of the image sensor 9000 can move to multiple positions ("image capturing positions"), relative to the radiation source 109. The image sensor 9000 may use the radiation detectors 100 and with the radiation from the radiation source 109 to capture images of multiple portions of the scene 50 respectively at the multiple positions. The image sensor 9000 can stitch these images to form an image of the entire scene 50. As shown in FIG. 7, according to an embodiment, the image sensor 9000 may include an actuator 500 configured to move the radiation detectors 100 to the multiple positions. The actuator 500 may include a controller 600. The actuator 500 may move the radiation detectors 100 to change their position relative to the collimator 2000 and move the collimator 2000 to change its position and orientation relative to the radiation detectors 100. The positions and orientations may be determined by the controller 600. After the radiation detectors 100 are moved to one of the image capturing positions, the collimator 2000 and the radiation detectors 100 may be aligned. For example, as shown in FIG. 6, the collimator 2000 and the radiation detectors 100 may be aligned by moving the radiation detectors 100 along a first direction 799X, moving the collimator 2000 in a second direction 799Y perpendicular to the first direction 799X, and rotating the collimator 2000 about an axis 799Z perpendicular to the first direction 799X and the second direction 799Y. The image capturing positions may be displaced from one another along the first direction 799X. In one embodiment, during operation to capture an image of a scene, the positions may be selected such that the active areas of the image sensor 9000 collectively tessellate the entire scene at the multiple positions.

FIG. 8 schematically shows that the image sensor 9000 can capture images of portions of the scene 50. In the example shown in FIG. 8, the radiation detectors 100 move to three positions A, B and C, for example, by using the actuator 500. Respectively at the positions A, B and C, the image sensor 9000 captures images 51A, 51B and 51C of portions of the scene 50. The image sensor 9000 can stitch the images 51A, 51B and 51C of the portions to form an image of the scene 50. The images 51A, 51B and 51C of the portions may have overlap among one another to facilitate stitching. Every portion of the scene 50 may be in at least one of the images captured when the detectors are at the multiple positions. Namely, the images of the portions when stitched together may cover the entire scene 50.

The radiation detectors 100 may be arranged in a variety of ways in the image sensor 9000. FIG. 9A schematically shows one arrangement, according to an embodiment, where the radiation detectors 100 are arranged in staggered rows. For example, radiation detectors 100J and 100K are in the same row, aligned in the Y direction, and uniform in size; radiation detectors 100C and 100D are in the same row, aligned in the Y direction, and uniform in size. Radiation detectors 100J and 100K are staggered in the X direction with respect to radiation detectors 100C and 100D. According to an embodiment, a distance X2 between two neighboring radiation detectors 100J and 100K in the same row is greater than a width X1 (i.e., dimension in the X direction, which is the extending direction of the row) of one detector in the same row and is less than twice the width X1. Radiation detectors 100J and 100E are in a same column, aligned in the X direction, and uniform in size; a distance Y2 between two neighboring radiation detectors 100J and 100E in the same column is less than a width Y1 (i.e., dimension in the Y direction) of one detector in the same column.

FIG. 9B schematically shows another arrangement, according to an embodiment, where the radiation detectors 100 are arranged in a rectangular grid. For example, the radiation detectors 100 may include radiation detectors 100J, 100K, 100E and 100F as arranged exactly in FIG. 9A, without radiation detectors 100C, 100D, 100G, or 100H in FIG. 9A.

Other arrangements may also be possible. For example, in FIG. 9C, the radiation detectors 100 may span the whole width of the image sensor 9000 in the X-direction, with a distance Y2 between two neighboring radiation detectors 100 being less than a width of one detector Y1. Assuming the width of the detectors in the X direction is greater than the width of the scene in the X direction, the image of the scene may be stitched from two images of portions of the scene captured at two positions spaced apart in the Y direction.

According to an embodiment, the radiation source 109 and the image sensor 9000 may collectively rotate around the object about multiple axes.

Figure 9D:
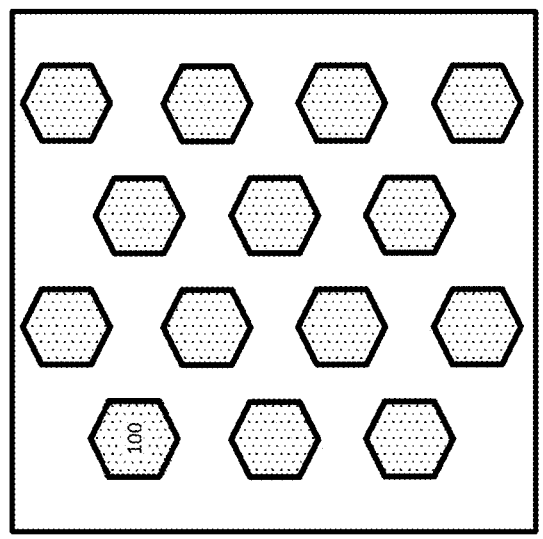

The radiation detectors 100 in the image sensor 9000 have any suitable sizes and shapes. According to an embodiment (e.g., in FIG. 9A-FIG. 9C), at least some of the radiation detectors 100 are rectangular in shape. According to an embodiment, as shown in FIG. 9D, at least some of the radiation detectors are hexagonal in shape. In such radiation detectors, the radiation detectors and the corresponding collimators that are aligned may have the same shape.

Figure 10:
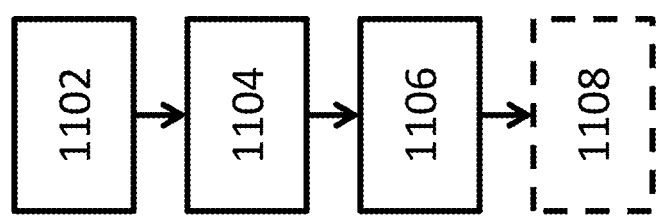
FIG. 10 schematically shows a flowchart of the method calibrating the apparatus, according to an embodiment.

FIG. 10 schematically shows a flowchart for a method of aligning the collimator 2000 and the radiation detectors 100, according to an embodiment. In procedure 1102, the radiation detectors 100 are moved along a first direction (e.g., the direction 799X in FIG. 6). The first direction may be in a plane in which the radiation detectors 100 are arranged. In procedure 1104, the collimator 2000 are moved along a second direction (e.g., the direction 799Y in FIG. 6) perpendicular to the first direction. The second direction may be in a plane in which the radiation detectors 100 are arranged. In procedure 1106, the collimator 2000 is rotated about an axis (e.g., axis 799Z in FIG. 6) perpendicular to the first direction and the second direction. In optional procedure 1108, the radiation detectors 100 are moved relative to the source 109, for example, to one of the image capturing positions.

Figure 11A:
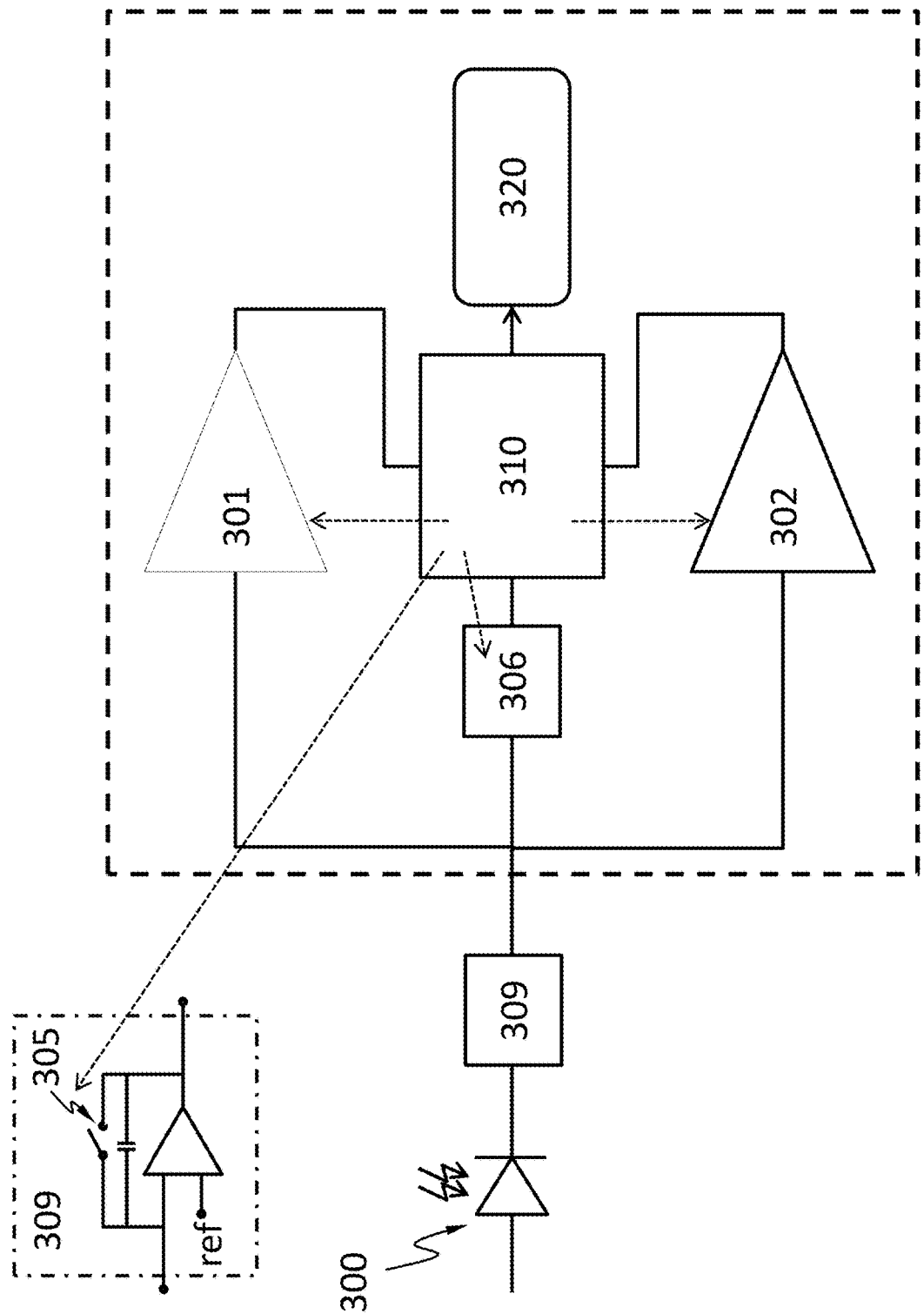
FIG. 11A and FIG. 11B each show a component diagram of an electronic system of the detector in FIG. 2A, FIG. 2B and FIG. 2C, according to an embodiment.
Figure 11B:
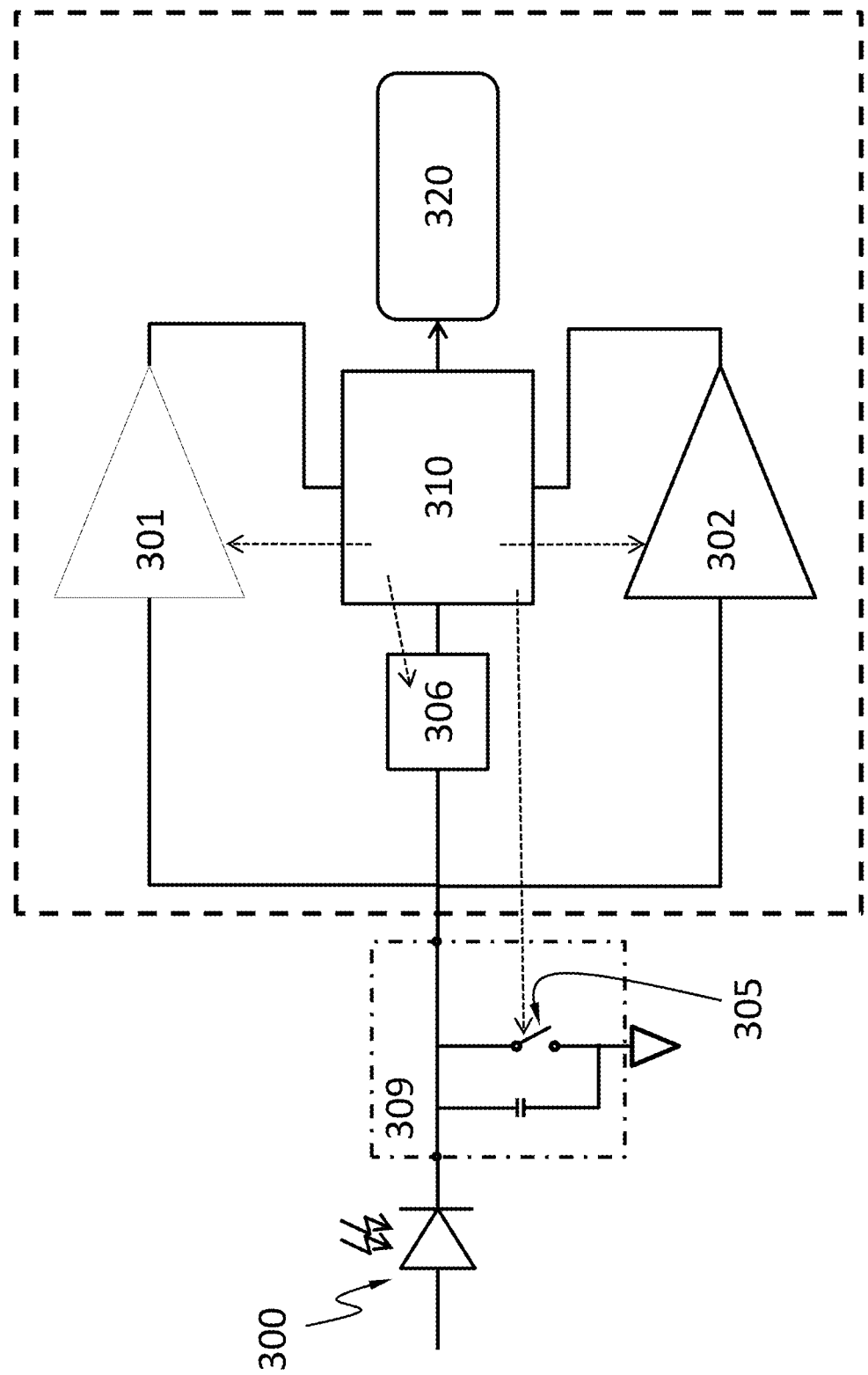

FIG. 11A and FIG. 11B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 configured as a continuous comparator reduces the chance that the system 121 misses signals generated by an incident particle of radiation. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident particles of radiation. When the incident radiation intensity is low, the chance of missing an incident particle of radiation is low because the time interval between two successive particles is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the maximum voltage one incident particle of radiation may generate in the diode or the resistor. The maximum voltage may depend on the energy of the incident particle of radiation (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activated or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{if } x \geq 0 \\ -x, \text{if } x \leq 0 \end{cases}.$$

The second threshold may be 200%-300% of the first threshold. The second threshold may be at least 50% of the maximum voltage one incident particle of radiation may generate in the diode or resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident radiation. However, having a high speed is often at the cost of power consumption.

The counter 320 is configured to register a number of particles of radiation reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cutting off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 12:
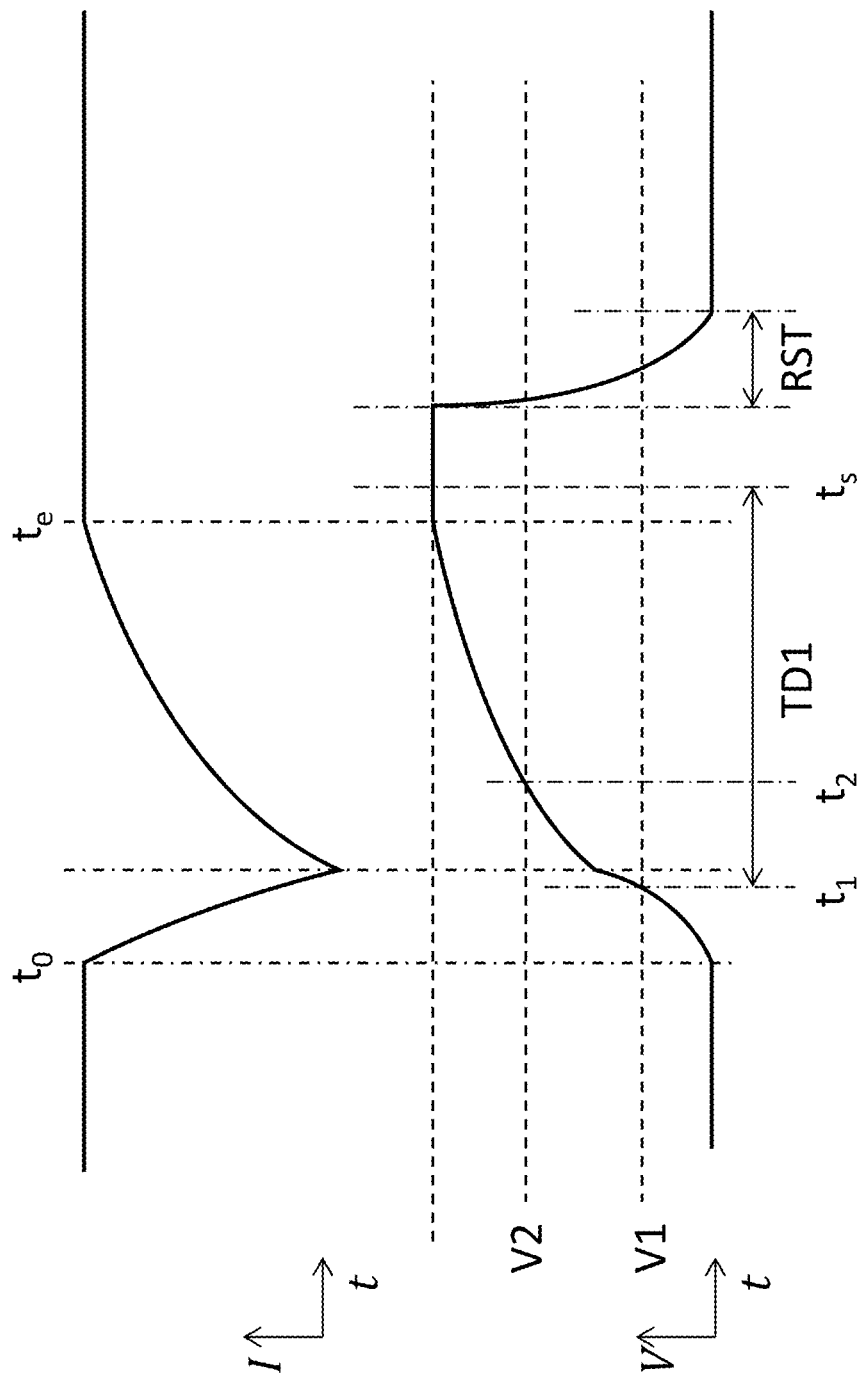
FIG. 12 schematically shows a temporal change of the electric current flowing through an electrode (upper curve) of a diode or an electrical contact of a resistor of a radiation absorption layer exposed to radiation, the electric current caused by charge carriers generated by a particle of radiation incident on the radiation absorption layer, and a corresponding temporal change of the voltage of the electrode (lower curve), according to an embodiment.

The system 121 may include an integrator 309 electrically connected to the electrode of the diode 300 or which electrical contact, wherein the integrator is configured to collect charge carriers from the electrode. The integrator can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 12, between $t_0$ to $t_1$, or $t_1$-$t_2$). After the integration period has expired, the capacitor voltage is sampled and then reset by a reset switch. The integrator can include a capacitor directly connected to the electrode.

FIG. 12 schematically shows a temporal change of the electric current flowing through the electrode (upper curve) caused by charge carriers generated by a particle of radiation incident on the diode or the resistor, and a corresponding temporal change of the voltage of the electrode (lower curve). The voltage may be an integral of the electric current with respect to time. At time to, the particle of radiation hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 causes the number registered by the counter 320 to increase by one. At time $t_e$, all charge carriers generated by the particle of radiation drift out of the radiation absorption layer 110. At time $t_s$, the time delay TD1 expires. In the example of FIG. 12, time $t_s$ is after time $t_e$; namely TD1 expires after all charge carriers generated by the particle of radiation drift out of the radiation absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by a particle of radiation, which relates to the energy of the particle of radiation. The controller 310 may be configured to determine the energy of the particle of radiation based on voltage the voltmeter 306 measures. One way to determine the energy is by binning the voltage. The counter 320 may have a sub-counter for each bin. When the controller 310 determines that the energy of the particle of radiation falls in a bin, the controller 310 may cause the number registered in the sub-counter for that bin to increase by one. Therefore, the system 121 may be able to detect a radiation image and may be able to resolve particle of radiation energies of each particle of radiation.

After TD1 expires, the controller 310 connects the electrode to an electric ground for a reset period RST to allow charge carriers accumulated on the electrode to flow to the ground and reset the voltage. After RST, the system 121 is ready to detect another incident particle of radiation. Implicitly, the rate of incident particles of radiation the system 121 can handle in the example of FIG. 12 is limited by 1/(TD1+ RST). If the first voltage comparator 301 has been deactivated, the controller 310 can activate it at any time before RST expires. If the controller 310 has been deactivated, it may be activated before RST expires.

The image sensor 9000 described above may be used in various detection systems, such as but not limited to, medical imaging such as dental Radiation radiography; a cargo scanning or non-intrusive inspection (NII) system for inspecting and identifying goods in transportation systems such as shipping containers, vehicles, ships, luggage, etc.; a full-body scanner; a radiation computed tomography (Radiation CT) system; an electron microscope; a system for performing energy-dispersive radiation spectroscopy (EDS).

The image sensor 9000 may also have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may also be suitable to use the image sensor 9000 in place of a photographic plate, a photographic film, a PSP plate, an radiation image intensifier, a scintillator, or another semiconductor radiation detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
 aligning a collimator and a plurality of radiation detectors of an image sensor by:
  moving the radiation detectors along a first direction;
  moving the collimator along a second direction perpendicular to the first direction;
  rotating the collimator about an axis perpendicular to the first direction and the second direction;
 wherein the plurality of radiation detectors are configured to capture images of portions of a scene at different image capturing positions, respectively, and to form an image of the scene by stitching the images of the portions.

2. The method of claim 1, wherein the image capturing positions are displaced from one another along the first direction.

3. The method of claim 2, further comprising moving the plurality of radiation detectors among the image capturing positions.

4. The method of claim 1, wherein the collimator includes a plurality of radiation transmitting zones and a radiation blocking zone, and
 wherein, when the collimator is aligned with the radiation detectors, the radiation blocking zone substantially blocks radiation that would otherwise incident on a dead zone of the image sensor and the radiation transmitting zones allow transmission of at least a portion of the radiation that would incident on active areas of the image sensor.

5. The method of claim 1, wherein at least some of the plurality of radiation detectors are arranged in staggered rows.

6. The method of claim 1, wherein active areas of the plurality of radiation detectors tessellate the scene at the positions.

7. The method of claim 1, wherein the images of portions of the scene at the different image capturing positions have a spatial overlap.

8. The method of claim 1, wherein the plurality of radiation detectors include a first radiation detector and a second radiation detector, respectively comprising a planar surface configured to receive radiation from a radiation source, and the planar surface of the first radiation detector and the planar surface of the second radiation detector are not parallel.

9. An image sensor comprising:
 a plurality of radiation detectors;
 a collimator; and
 an actuator configured to:
  move the radiation detectors along a first direction;
  move the collimator along a second direction perpendicular to the first direction;
  rotate the collimator about an axis perpendicular to the first direction and the second direction;
 wherein the plurality of radiation detectors are configured to capture images of portions of a scene at different image capturing positions, respectively, and to form an image of the scene by stitching the images of the portions.

10. The image sensor of claim 9, wherein the image capturing positions are displaced from one another along the first direction.

11. The image sensor of claim 9, wherein the collimator includes a plurality of radiation transmitting zones and a radiation blocking zone, and
 wherein, when the collimator is aligned with the radiation detectors, the radiation blocking zone substantially blocks radiation that would otherwise incident on a dead zone of the image sensor and the radiation transmitting zones allow transmission of at least a portion of the radiation that would incident on active areas of the image sensor.

12. The image sensor of claim 9, wherein at least some of the plurality of radiation detectors are arranged in staggered rows.

13. The image sensor of claim 9, wherein active areas of the plurality of radiation detectors tessellate the scene at the image capturing positions.

14. The image sensor of claim 9, wherein the images of portions of the scene at the different image capturing positions have a spatial overlap.

15. The image sensor of claim 9, wherein the plurality of radiation detectors include a first radiation detector and a second radiation detector, respectively comprising a planar surface configured to receive radiation from a radiation source, and the planar surface of the first radiation detector and the planar surface of the second radiation detector are not parallel.

16. The image sensor of claim 15, wherein a relative position of the first radiation detector with respect to the second radiation detector remains the same.

17. A radiation computed tomography system comprising: the image sensor of claim 9, and a radiation source.

* * * * *